United States Patent [19]

Uhl et al.

[11] 4,225,608
[45] Sep. 30, 1980

[54] PHENOXY HETEROCYCLIC AMINES AND USE THEREOF

[75] Inventors: Jürgen Uhl; Dieter Marx; Hans-Heinrich Hausberg; Wighard Strehlow; Klaus-Otto Minck; Helmut Müller-Calgan; Christoph Seyfried, all of Darmstadt, Fed. Rep. of Germany

[73] Assignee: Merck Patent Gesellschaft mit beschränkter Haftung, Darmstadt, Fed. Rep. of Germany

[21] Appl. No.: 21,277

[22] Filed: Mar. 16, 1979

[30] Foreign Application Priority Data

Mar. 18, 1978 [DE] Fed. Rep. of Germany ....... 2811952

[51] Int. Cl.$^3$ .................. C07D 211/22; C07D 207/08; A61K 31/40; A61K 31/445
[52] U.S. Cl. .................................... 424/267; 424/244; 424/274; 260/239 B; 260/239 BF; 260/326.47; 260/326.5 S; 260/326.5 M; 546/230; 546/236; 546/238; 546/240
[58] Field of Search ............... 546/236, 230, 238, 240; 260/326.5 M, 239 B, 239 BF, 326.47, 326.5 S; 424/244, 267, 247

[56] References Cited

U.S. PATENT DOCUMENTS 3,709,892  1/1973  Leeming ..................... 260/326.5 M Primary Examiner—Henry R. Jiles
Assistant Examiner—R. W. Ramsuer
Attorney, Agent, or Firm—Millen & White

[57] ABSTRACT

Phenoxyalkylamines of the formula

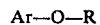

Ar—O—R wherein Ar is phenyl or phenyl which is monosubstituted or disubstituted by F, Cl, Br, alkyl or alkoxy each of 1–4 carbon atoms, cycloalkoxy of 3–6 carbon atoms, $CF_3$, CN, alkylthio of 1–4 carbon atoms, $SCF_3$, OH and/or alkanoyloxy with 1–10 carbon atoms; R is (1-$R^1$-2-pyrrolidyl)—$CH_2$—$CHR^2$—, (1-$R^1$-2-piperidyl)-$CH_2$—$CHR^2$— or 1-$R^1$-3-Z-4-hexahydroazepinyl; $R^1$ is H, alkyl or alkenyl each of up to 4 carbon atoms, cyclopropylmethyl or benzyl; $R^2$ is H, alkyl of 1–4 carbon atoms or phenyl; and Z is alkyl of 1–4 carbon atoms with the proviso that Ar is p-fluorophenyl only if R is not 2-(1-methyl-2-piperidyl)-ethyl; and the physiologically acceptable acid addition salts thereof, possess valuable pharmacological properties, e.g., are antidepressants.

6 Claims, No Drawings

PHENOXY HETEROCYCLIC AMINES AND USE THEREOF

The present invention relates to phenoxyalkylamines having pharmaceutical properties.

SUMMARY OF THE INVENTION

It is an object of this invention to provide new compounds having pharmacological properties.

Upon further study of the specification and appended claims, further objects and advantages of this invention will become apparent to those skilled in the art.

These objects have been achieved by providing new phenoxyalkylamines of the formula I

$$Ar-O-R \qquad \qquad I$$

wherein Ar is phenyl or phenyl which is monosubstituted or disubstituted by F, Cl, Br, alkyl or alkoxy each of 1–4 carbon atoms, cycloalkoxy of 3–6 carbon atoms, $CF_3$, CN, alkylthio of 1–4 carbon atoms, $SCF_3$, OH and/or alkanoyloxy of 1–10 carbon atoms; R is $(1-R^1-2\text{-pyrrolidyl})-CH_2-CHR^2-$, $(1-R^1-2\text{-piperidyl})-CH_2-CHR^2-$ or $1-R^1-3\text{-Z-4-hexahydroazepinyl}$; $R^1$ is H, alkyl or alkenyl each of up to 4 carbon atoms, cyclopropylmethyl or benzyl; $R^2$ is H, alkyl of 1–4 carbon atoms or phenyl; and Z is alkyl of 1–4 carbon atoms; with the proviso that Ar is p-fluorophenyl only when R is not 2-(1-methyl-2-piperidyl)-ethyl; and their physiologically acceptable acid addition salts.

DETAILED DISCUSSION

The present invention relates to the phenoxyalkylamines of formula I and their physiologically acceptable acid addition salts.

In the radicals Ar, $R^1$, $R^2$ and Z, alkyl is preferably methyl, and also ethyl, n-propyl, isopropyl, n-butyl, isobutyl, sec-butyl or tert-butyl. Alkoxy is preferably methoxy, and also ethoxy, n-propoxy, isopropoxy, n-butoxy, isobutoxy, sec-butoxy or tert-butoxy. Cycloalkoxy is preferably cyclopentyloxy or cyclohexyloxy, and also cyclopropyloxy, cyclobutyloxy, 1-, 2-, or 3-methylcyclobutyloxy or 1-, 2- or 3-methylcyclopentyloxy. Alkylthio is preferably methylthio, but also ethylthio, n-propylthio, isopropylthio, n-butylthio, isobutylthio, sec-butylthio or tert-butylthio. Alkanoyloxy is preferably unbranched and is preferably acetoxy, propionyloxy, butyryloxy, valeryloxy, hexanoyloxy, heptanoyloxy, octanoyloxy, nonanoyloxy or decanoyloxy; and also, for example, formyloxy, isobutyryloxy, isovaleryloxy, methylethylacetoxy, trimethylacetoxy or isohexanoyloxy. Alkenyl is preferably allyl, and also vinyl, propenyl, isopropenyl, 1-buten-1- or -2-yl, 2-buten-1- or -2-yl, 3-buten-1- or -2-yl, 2-methyl-1-propen-1- or -2-yl or 2-methyl-2-propen-1-yl.

When Ar is a substituted phenyl group, it is preferably monosubstituted. It can, however, also be disubstituted, in which case the substituents can be identical or different. Preferred substituents on the phenyl group are F, Cl, Br, methyl, methoxy, cyclopentyloxy, trifluoromethyl and methylthio. In detail, Ar is preferably phenyl, o-, m- or p-fluorophenyl, o-, m- or p-chlorophenyl, o-, m- or p-bromophenyl, o-, m- or p-tolyl, o-, m- or p-methoxyphenyl, o-, m- or p-cyclopentyloxyphenyl, o-, m- or p-trifluoromethylphenyl, o-, m- or p-methylthiophenyl; and also, for example, o-, m- or p-ethylphenyl, o-, m- or p-n-propylphenyl, o-, m- or p-isopropylphenyl, o-, m- or p-n-butylphenyl, o-, m- or p-isobutylphenyl, o-, m- or p-ethoxyphenyl, o-, m- or p-n-propoxyphenyl, o-, m- or p-isopropoxyphenyl, o-, m- or p-butoxyphenyl, o-, m- or p-isobutoxyphenyl, o-, m- or p-cyclopropyloxyphenyl, o-, m- or p-cyclohexyloxyphenyl, o-, m- or p-cyanophenyl, o-, m- or p-ethylthiophenyl, o-, m- or p-n-propylthiophenyl, o-, m- or p-isopropylthiophenyl, o-, m- or p-n-butylthiophenyl, o-, m- or p-isobutylthiophenyl, o-, m- or p-trifluoromethylthiophenyl, o-, m- or p-hydroxyphenyl, o-, m- or p-acetoxyphenyl, o-, m- or p-propionyloxyphenyl, o-, m- or p-butyryloxyphenyl, o-, m- or p-isobutyryloxyphenyl, o-, m- or p-valeryloxyphenyl, o-, m- or p-hexanoyloxyphenyl, o-, m- or p-heptanoyloxyphenyl, o-, m- or p-octanoyloxyphenyl, o-, m- or p-nonanoyloxyphenyl or o-, m- or p-decanoyloxyphenyl; and also dihalogenophenyl, such as 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-fluoro-4-chlorophenyl or 2-bromo-4-chlorophenyl; dimethylphenyl, such as 2,3-, 2,4-, 2,5-, 2,6-, 3,4- or 3,5-dimethylphenyl; dimethoxyphenyl, such as 2,3-, 2,4-, 2,5-, 2,6-, 3,4- or 3,5-dimethoxyphenyl; hydroxy-chlorophenyl, such as 2-hydroxy-4-chlorophenyl or 3-hydroxy-4-chloro-phenyl; alkanoyloxy-chlorophenyl, especially 2-alkanoyloxy-4-chlorophenyl, such as 2-acetoxy-, 2-propionyloxy-, 2-butyryloxy-, 2-valeryloxy-, 2-hexanoyloxy-, 2-heptanyloxy-, 2-octanoyloxy-, 2-nonanoyloxy- or 2-decanoyloxy-4-chlorophenyl; or alkoxy-trifluoromethyl-phenyl, especially methoxy-trifluoromethyl-phenyl, such as 2-methoxy-5-trifluoromethylphenyl.

The radical $R^1$ is preferably H or methyl, and also ethyl, n-propyl, allyl, cyclopropylmethyl or benzyl. The radical $R^2$ is preferably H, and also methyl or phenyl.

Accordingly, the radical R is preferably 2-(2-pyrrolidyl)ethyl, 2-(1-methyl-2-pyrrolidyl)-ethyl, 2-(2-piperidyl)-ethyl or 2-(1-methyl-2-piperidyl)-ethyl; and also, for example, 2-(1-ethyl-, 2-(1-n-propyl-, 2-(1-allyl-, 2-(1-cyclopropylmethyl- or 2-(1-benzyl-2-pyrrolidyl)-ethyl, 2-(1-ethyl-, 2-(1-n-propyl-, 2-(1-allyl-, 2-(1-cyclopropylmethyl- or 2-(1-benzyl-2-piperidyl)-ethyl, 1-methyl-2-(2-pyrrolidyl)-ethyl, 1-phenyl-2-(2-pyrrolidyl)-ethyl, 1-methyl-2-(1-methyl-2-pyrrolidyl)ethyl, 1-phenyl-2-(1-methyl-2-pyrrolidyl)-ethyl, 1-methyl-2-(2-piperidyl)-ethyl, 1-phenyl-2-(2-piperidyl)-ethyl, 1-methyl-2-(1-methyl-2-piperidyl)-ethyl, 1-phenyl-2-(1-methyl-2-piperidyl)ethyl or 3-methyl- or 1,3-dimethyl-4-hexahydroazepinyl.

Accordingly, the invention relates in particular to those compounds of formula I in which at least one of the defined radicals has one of the meanings indicated above, especially one of the preferred meanings indicated above. Some preferred groups of compounds can be expressed by the following partial formulae Ia to Ie, which correspond to the formula I and in which the radicals not specified in more detail are as defined for formula I, but in which in Ia Ar is phenyl, fluorophenyl, chlorophenyl, bromophenyl, tolyl, methoxyphenyl, cyclopentyloxyphenyl, trifluoromethylphenyl, methylthiophenyl or hydroxyphenyl in Ib Ar is phenyl, p-fluorophenyl, o- or p-chlorophenyl, o- or p-bromophenyl, p-tolyl, o- or p-methoxyphenyl, o-cyclopentyloxyphenyl, m-trifluoromethylphenyl, p-methylthiophenyl or p-hydroxyphenyl;

in Ic
R is 2-(1-methyl-2-pyrrolidyl)-ethyl, 2-(2-piperidyl)ethyl, 2-(1-methyl-2-piperidyl)-ethyl, 1-phenyl-2-(1-methyl-2-piperidyl)-ethyl or 1,3-dimethyl-4-hexahydroazepinyl;

in Id
Ar is phenyl, p-fluorophenyl, o- or p-chlorophenyl, o- or p-bromophenyl, p-tolyl, o- or p-methoxyphenyl, o-cyclopentyloxyphenyl, m-trifluoromethylphenyl, p-methylthiophenyl or p-hydroxyphenyl and R is 2-(1-methyl-2-pyrrolidyl)-ethyl, 2-(2-piperidyl)ethyl, 2-(1-methyl-2-piperidyl)-ethyl, 1-phenyl-2-(1-methyl-2-piperidyl)-ethyl or 1,3-dimethyl-4-hexahydroazepinyl; and in Ie
Ar is p-fluorophenyl, p-chlorophenyl, p-methoxyphenyl, m-trifluoromethylphenyl or p-methylthiophenyl and R is 2-(1-methyl-2-pyrrolidyl)-ethyl, 2-(2-piperidyl)ethyl, 2-(1-methyl-2-piperidyl)-ethyl or 1,3-dimethyl-4-hexahydroazepinyl.

The compounds of formula I possess at least one asymmetric carbon atom. They can therefore be in the form of racemates or, if several asymmetric carbon atoms are present, also in the form of mixtures of several racemates, as well as in various optically active forms.

The present invention also relates to a process for the preparation of the compounds of formula I and of their physiologically acceptable acid addition salts, which comprises (a) reacting a phenol of formula II

Ar—OH      II in which Ar is as defined above, or one of its salts with a compound of formula III

X—R      III in which X is Cl, Br, I or OH and R is as defined above, or with one of its reactive derivatives, or (b) treating with a reducing agent a compound of formula IV

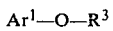
Ar$^1$—O—R$^3$      IV in which Ar$^1$ is Ar or a radical reducible to Ar and R$^3$ is R or a radical reducible to R and Ar and R are as defined above, but in which Ar$^1$ is not Ar when R$^3$ is R; and (c) optionally, in a resulting compound of formula I converting a secondary amino group by treatment with an alkylating, alkenylating, cyclopropylmethylating or benzylating agent into the corresponding tertiary amino group; or converting an N-benzyl group by treatment with a reducing agent into a NH group; and/or converting a phenolic hydroxyl group by treatment with an alkylating, cycloalkylating or alkanoylating agent into the corresponding alkoxy, cycloalkoxy or alkanoyloxy group; and/or (d) converting a resulting base of formula I by treatment with an acid into one of its physiologically acceptable acid addition salts.

In other respects, the compounds of formula I are prepared according to methods which are in themselves known, such as are described in the literature (for example in the standard works such as Houben-Weyl, Methoden der Organischen Chemie (Methods of Organic Chemistry), Georg-Thieme-Verlag, Stuttgart; and Organic Reactions, John Wiley & Sons, Inc., New York), and specifically under reaction conditions which are known and suitable for the mentioned reactions. It is also possible to make use of variants which are in themselves known and are not mentioned in more detail here.

The starting materials of the formulae II to IV can, if desired, also be formed in situ, wherein they are not isolated from the reaction mixture but are immediately further reacted to give the compounds of formula I.

The compounds of formula I are preferably obtained by reacting the phenols of formula Ar—OH (II), or, preferably, their salts, with the compounds of formula X—R (III).

As a rule, the phenols of formula II are known. When they are new, they can be prepared according to methods which are in themselves known, for example, by splitting corresponding benzyl or methyl ethers.

In the bases of formula III, the radical X is preferably Cl or Br. Reactive derivatives of the bases of formula III are, in particular, the reactive esters of the alcohols of formula III (X=OH), preferably the corresponding alkylsulfonates (in which the alkyl group has 1–6 carbon atoms) and the corresponding arylsulfonates (in which the aryl group has 6–10 carbon atoms), for example, the corresponding methane-, benzene, p-toluene- or naphthalene-1- or -2-sulfonates.

Some of the bases of formula III are known. The bases of formula III not known hitherto can be prepared by methods which are in themselves known, analogously to known compounds. Thus, the compounds of formula III (K=OH) are obtainable, for example, by reduction of corresponding esters or ketones of the (1-R$^1$-2-pyrrolidyl)—CH$_2$—COO—alkyl, (1-R$^1$-2-pyrrolidyl)—CH$_2$—CO—R$^2$, (1-R$^1$-2-piperidyl)—CH$_2$—COO—alkyl, (1-R$^1$-2-piperidyl)—CH$_2$—CO—R$^2$ or 1-R$^1$-3-Z-hexahydroazepin-4-one type; the compounds of formula III (X=Cl, Br or I) are obtainable from the alcohols and inorganic halides, such as SOCl$_2$, PBr$_3$ or HI; and the sulfonates are obtainable by esterification of the alcohols with the corresponding sulfonyl chlorides.

The tertiary amines among the amines of formula II (in which R$^1$ is not H) are also accessible from the secondary amines (III, R$^1$=H) by alkylation, alkenylation, cyclopropylmethylation or benzylation. Conversely, the secondary amines (III, R$^1$=H) can be obtained from the corresponding N-alkyl derivatives (III, R$^1$=alkyl with 1-4 carbon atoms) by dealkylation with ethyl chloroformate. Furthermore, the amines of the formula III can be prepared by reduction of corresponding pyridines, pyrroles or azepines. Thus, for example, 2-methylpyridine can be metallized with C$_6$H$_5$Li and then reacted with benzaldehyde to give 1-phenyl-2-(2-pyridyl)-ethanol and the latter can be reduced to 1-phenyl-2-(2-piperidyl)-ethanol. In a similar manner, 1-phenyl-2-(1-methyl-2-pyrrolidyl)-ethanol can be obtained by reacting 2-hydroxymethylpyrrolidine with SOCl$_2$ and then carrying out a Leuckart-Wallach methylation to give 1-methyl-2-chloromethyl-pyrrolidine, converting the latter to the Grignard derivative and reacting this derivative with benzaldehyde. 1,3-Dimethyl-4-hydroxy-hexadydroazepine is accessible by expanding the ring of 1,3-dimethyl-4-piperidone with CH$_2$N$_2$ to give 1,3-dimethyl-hexahydroazepin-4-one and reducing the latter with NaBH$_4$.

Prior to the reaction with III, the phenol II is preferably first converted into a salt, especially into a metal salt, for example, an alkali metal salt (Li, Na or K salt). The phenol can be reacted with a metal salt-forming reagent, for example, an alkali metal (for example, Na), an alkali metal hydride or alkali metal amide (for example, LiH, NaH, $NaNH_2$ or $KNH_2$), an alkali metal alcoholate (in which the alcohol part preferably has 1-4 carbon atoms, for example, lithium methylate, ethylate or tert-butylate, sodium methylate, ethylate or tert-butylate or potassium methylate, ethylate or tert-butylate), an organometallic compound (for example, butyl-lithium, phenyl-lithium or phenylsodium) or a hydroxide, carbonate or bicarbonate of a metal (for example, of Li, Na, K or Ca). The preparation of the phenolate is advantageously carried out in the presence of a solvent or solvent mixture. Suitable solvents are, for example, hydrocarbons (such as hexane, benzene, toluene or xylene), halogenated hydrocarbons (such as $CH_2Cl_2$, $CHCl_4$ or $CCl_4$), ethers (such as diethyl ether, diisopropyl ether, tetrahydrofuran (THF), dioxane or diethylene glycol dimethyl ether), amides (such as dimethylformamide (DMF)), alcohols (such as methanol or ethanol) or ketones (such as acetone or butanone).

The phenol II or its salt is preferably reacted with the compound III in the presence of a diluent, for example, that solvent which has been used for the preparation of the salt; however, this solvent can be replaced by another solvent or diluted with another solvent. A particular varient comprises carrying out the reaction in a two-phase system (for example, in $CH_2Cl_2$/aqueous sodium hydroxide solution), and a catalyst (for example, a crown ether, an ammonium salt such as a trialkylbenzylammonium halide, or a phosphonium salt) can also be added. The reaction is as a rule carried out at temperatures between about −20° and 150° C. and preferably between 20° and 120° C.

The phenolate can also be formed in situ. In this case, the phenol II and the compound III are allowed to react with one another in the presence of a base.

The compounds of formula I are also obtainable by reduction of the compounds of formula IV. In a compound of formula IV, at least one of the two radicals $Ar^1$ and $R^3$ is reducible to Ar or, respectively, to R, so that the formula IV comprises the general partial formulae IVa, IVb and IVc

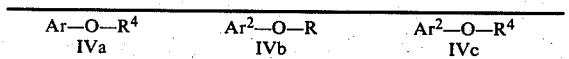

| $Ar$—$O$—$R^4$ | $Ar^2$—$O$—$R$ | $Ar^2$—$O$—$R^4$ |
| --- | --- | --- |
| IVa | IVb | IVc | in which $Ar^2$ is a radical reducible to Ar and $R^4$ is a radical reducible to R and Ar and R are as defined.

The radical $Ar^2$ is preferably a phenyl group which is monosubstituted or polysubstituted by benzyloxy and which can also contain one or more further substituents and is in particular o-, m- or p-benzyloxyphenyl or 2-benzyloxy-4-chloro-phenyl.

The radical $R^4$ differs from the radical R in that it has (preferably 1-4) additional C-C and/or C-N multiple bonds and/or in that one or more (preferably 1-3) reducible groups, especially carbonyl groups, are present in place of $CH_2$ groups. Preferred radicals $R^4$ are, for example, (2-pyridyl)—$CH_2$—$CHR^2$— and (1-$R^1$-3-, -4-, -5- or -6-oxo-2-piperidyl-$CH_2$—$CHR^2$ and also (1-$R^1$-2-pyrryl)—$CH_2$—$CHR^2$—, (1-$R^1$-3-, -4-, or -5-oxo-2-pyrrolidyl)—$CH_2$—$CHR^2$—, (1-$R^1$-2-pyrrolidyl)—$CO$—$CHR^2$—, (1-$R^1$-2-pyrrolidyl)—$CH_2$—$CO$—, (1-$R^1$-2-piperidyl)—$CO$—$CHR^2$—, (1-$R^1$-2-piperidyl)—$CH_2$—$CO$—, 1-$R^1$-3-Z-4-azepinyl, 1-$R^1$-3-Z-2-, -5-, -6- or -7-oxo-hexahydroazepinyl.

As a rule, the starting materials of formula IV are new. However, they are easily obtainable analogously to known compounds by methods which are in themselves known, preferably by reaction of the phenols of the formula $Ar^1$—OH, most of which are known, or of their salts, with compounds of formula X—$R^3$ (in which $Ar^1$, X and $R^3$ are as defined above). The compounds of formula X—$R^3$ can be prepared analogously to the compounds of formula III.

The starting materials of formula IV can, for example, be converted to the compounds of formula I by catalytic hydrogenation, with nascent hydrogen, with complex metal hydrides or with the aid of other chemical reducing agents, the correspondingly appropriate compounds of formula IV, thus being equivalent in this sense. The reduction methods which are most suitable for the individual starting materials are generally dependent on the nature of the reducible group $Ar^2$ or $R^4$ and are well known to those skilled in the art from the information given in the literature. Thus, for example, pyridine derivatives and benzyl ethers can particularly advantageously be hydrogenated catalytically. A reduction of lactams, on the other hand, is particularly advantageously carried out with complex metal hydrides or with diborane.

Catalysts suitable for catalytic hydrogenation reactions include, for example, noble metal catalysts, nickel catalysts or cobalt catalysts, and also mixed catalysts such as copper/chromium oxide. Noble metals which can be used, in particular, platinum and palladium and these can be on supports (for example, on charcoal, calcium carbonate or strontium carbonate), in the form of oxides (for example, platinum oxide) or in a finely divided form. Nickel catalyst and cobalt catalysts are preferably employed in the form of Raney metals. The hydrogenation can preferably be carried out under pressures of between about 1 and 200 atmospheres and at temperatures between about −80° and +150° C. and preferably between 20° and 100° C. The hydrogenation is carried out in the presence of an inert solvent, for example, an alcohol, such as methanol, ethanol or isopropanol, a carboxylic acid, such as acetic acid, an ester, such as ethyl acetate, or an ether, such as THF or dioxane. Solvent mixtures can also be used, for example, including mixtures containing water. Furthermore, it can be advantageous to add a base, such as sodium hydroxide or potassium hydroxide or ammonia, during the hydrogenation.

Furthermore, complex metal hydrides such as $LiAlH_4$, $NaBH_4$ or $NaAl(OCH_2CH_2OCH_3)_2H_2$ and also diborane can be employed as reducing agents, if desired with the addition of catalysts such as $BF_3$, $AlCl_3$ or LiBr. Suitable solvents for these reactions are, in particular, ethers, such as diethyl ether, THF, dioxane, 1,2-dimethoxyethane or diglymes, and also hydrocarbons, such as benzene. For a reduction with $NaBH_4$, suitable solvents are, in particular, alcohols such as methanol or ethanol. With this method, the reduction is preferably carried out at temperatures between about −80° and +150° C. and in particular between about 20° and 120° C.

A further suitable reduction method is the reaction with nascent hydrogen. The latter can be produced, for example, by treating metals with acids or bases. Thus, for example, the systems zinc/acid, zinc/alkali metal hydroxide solution, iron/acid or tin/acid can be used. Suitable acids include, for example, hydrochloric acid or acetic acid. An alkali metal, such as sodium, in an alcohol, such as ethanol, isopropanol, n-butanol, amyl alcohol or isoamyl alcohol, or in phenol can also be used as a reducing agent, as can also, for example, an aluminum/nickel alloy in alkaline-aqueous or alkaline-aqueous-alcoholic solution and sodium amalgam or aluminum amalgam in aqueous-alcoholic or aqueous solution. For these methods, the reaction temperatures are between about 0° and 150° C. and preferably between about 20° and 120° C.

The starting compounds of formula IV can also be converted to compounds of formula I by cathodic reduction, preferably in an aqueous-alcoholic or aqueous-acetic acid medium. Further suitable reducing agents are, for example, sodium dithionite in aqueous-alcoholic or alkaline solution and also iron-II hydroxide, tin-II chloride, hydrogen sulfide, hydrogen sulfides, sulfides, polysulfides and hydrazine, all of which are used in accordance with the conditions quoted in the literature for such reductions.

Furthermore, if desired, a resulting secondary amine of formula I ($R^1$=H) can be alkylated at the nitrogen atom, tertiary amines of formula I ($R^1$=alkyl of 1–4 carbon atoms) being obtained. Suitable N-alkylating agents are, for example, the corresponding alkyl halides, for example, methyl chloride, methyl bromide, methyl iodide, ethyl chloride, ethyl bromide, ethyl iodide, n-propyl chloride, n-propyl bromide or n-propyl iodide and the like, and also the corresponding dialkyl sulfates, such as dimethyl sulfate, and the corresponding sulfonic acid alkyl esters, such as methyl p-toluenesulfonate. A methyl group can also, for example, be introduced by treatment with formic acid and aqueous formaldehyde solution, preferably by heating for several hours at temperatures between 50° and 100° C. In general, the N-alkylation is preferably carried out in the presence or absence of an inert solvent at temperatures between about 0° and about 120° C. and preferably between 40° and 100° C., it being possible for a catalyst, preferably a base, such as potassium tert-butylate, also to be present.

An alkylation is also effected by treating a secondary base I ($R^1$=H) with an aldehyde or ketone in the presence of hydrogen and a hydrogenation catalyst (for example Raney nickel) at temperatures between about 50° and 100° C. and under pressures of between about 1 and 200 atmospheres; using acetone, the corresponding isopropyl compound I ($R^1$=isopropyl) is obtained in this way.

It is also possible to carry out an alkylation as a multistage reaction. For example, a compound of the formula I ($R^1$=H) can first be acylated in a manner which is in itself known (for example, acetylated by treatment with acetic anhydride/pyridine) and the resulting N-acylation product (for example N-acetylation product) can then be reduced to the desired tertiary amine, for example with a complex metal hydride such as LiAlH$_4$ in an inert solvent such as diethyl ether or THF, preferably at temperatures between 20° and 60° C.

In an entirely analogous manner, a secondary amine of formula I ($R^1$=H) can be treated with alkenylating, cyclopropylmethylating or benzylating agents (for example, alkenyl halides such as allyl chloride or allyl bromide, cyclopropylmethyl halides, such as cyclopropylmethyl chloride or cyclopropylmethyl bromide, or benzyl halides, such as benzyl chloride or benzyl bromide), whereupon compounds of formula I ($R^1$=alkenyl of up to 4 carbon atoms, cyclopropylmethyl or benzyl) are formed.

Furthermore, in a compound of formula I ($R^1$=benzyl), the benzyl group can be removed reductively by one of the abovementioned methods, preferably by hydrogenolysis in the presence of a noble metal catalyst.

Furthermore, in a resulting compound of formula I, phenolic hydroxyl groups can be alkylated, cycloalkylated or acylated. Suitable alkylating agents are, for example, the above-mentioned alkyl halides, dialkyl sulfates and sulfonic acid alkyl esters, suitable cycloalkylating agents are the corresponding cycloalkyl halides (for example cyclopropyl chloride, cyclopropyl bromide, or cyclopropyl iodide, cyclobutyl chloride, cyclobutyl bromide or cyclobutyl iodide, cyclopentyl chloride, cyclopentyl bromide or cyclopentyl iodide or cyclohexyl chloride, cyclohexyl bromide or cyclohexyl iodide) and suitable acylating agents include the corresponding fatty acids (for example, formic acid, acetic acid, propionic acid, butyric acid, valeric acid, capric acid, hexanoic acid, heptanoic acid, octanoic acid, nonanoic acid or decanoic acid) and also their halides, especailly their chlorides and bromides, and their anhydrides. These reactions are preferably carried out at temperatures between about 0° and about 150° C. and preferably between 20° and 100° C. in an inert solvent, for example, an alcohol, such as methanol or ethanol, a hydrocarbon, such as benzene, an amide, such as DMF, an ether, such as THF, or an amine, such as pyridine. If halides or anhydrides are used, the reaction is preferably carried out in the presence of a base, such as NaOH, KOH, triethylamine or pyridine, it being possible for an excess of this base to serve as the solvent. Acylation reactions with the free fatty acids succeed preferalby in the presence of a dehydrating agent, such as carbonyldiimidazole or dicyclohexyl carbodiimide.

A resulting base of formula I can be converted by means of an acid into the corresponding acid addition salt. Suitable acids for this reaction are those which result in physiologically acceptable salts. Thus, it is possible to use inorganic acids, for example, sulfuric acid, hydrogen halide acids, such as hydrochloric acid or hydrobromic acid, phosphoric acids, such as orthophosphoric acid, nitric acid or sulfamic acid, and also organic acids, in detail, aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, and laurylsulfuric acid.

The free bases of the formula I can, if desired, be liberated from their salts by treatment with strong bases, such as sodium hydroxide or potassium hydroxide, sodium carbonate or potassium carbonate.

It has been found that the compounds of formula I and their physiologically acceptable acid addition salts possess valuable pharmacological properties. Thus, in particular, they display effects on the central nervous system, above all antidepressive effects. In detail, they have, for example, reserpineantagonistic action (detectable, for example, against reserpine in mice, on the basis of the method of Askew, Life Science, Volume 10, (1963), pages 725-730); an anticataleptic action (detectable, for example, against tetrabenazine in rats, on the basis of the method of Giurgea et al, Medicina Experimentalis, Volume 9, (1963), pages 249-262); and an antiptotic action (detectable, for example, against reserpine on the basis of the method of Domenjoz and Theobald, Arch. int. pharmacodyn., Volume 120, (1959), page 450 et seq., with evaluation according to Rubin et al, J. Pharmacol. Exp. Therap., Volume 120 (1957), pages 125-136). Moreover, they boost the action of 5-hydroxytryptophan in mice (method: similar to that of Ross et al, Acta pharmacol. et toxicol., Volume 39 (1976), pages 152-166) and increase and/or prolong the effects on the central nervous system of stimulation and a rise in temperature initiated by D-amphetamine sulfate (for example 1.5 mg/kg, subcutaneously, administered 1 hour after the test substance, which is also administered subcutaneously) and aggregation (placing 5 rats in one glass) (method according to Müller-Calgan et al in Zippel, H. P. (Editor): Memory and Transfer of Information, Plenum Press, New York—London, 1973, pages 87-125). The substances also have an influence on the biogenic amines of the central nervous system. Thus, for example, they lead in vitro to the inhibition of the uptake of noradrenaline, 5-hydroxy-tryptamine and dopamine (method: Kannengiesser et al, Biochem. Pharmacol., Volume 22 (1973), pages 73-84) in synapses and in vivo inhibit (method: Carlsson et al, Europ. J. Pharmacol., Volume 5 (1969), pages 357-366; 367-373) the liberation of catecholamine and serotonin induced in the brain by tyramine derivatives.

Compounds of formula I and their physiologically acceptable acid addition salts can therefore be used as medicaments and also as intermediates for the preparation of other medicinal active compounds.

Thus, the invention also relates to the use of the compounds of formula I and their physiologically acceptable salts for the preparation of pharmaceutical formulations, especially by a non-chemical route. To prepare such formulations, the compounds can be brought, together with at least one excipient or auxiliary and optionally in combination with one or more further active ingredients, into a suitable dosage form.

The invention also relates to agents, especially pharmaceutical formulations, containing a compound of formula I and/or one of its physiologically acceptable acid addition salts. These formulations can be employed as medicaments in human medicine or veterinary medicine, e.g., to treat mammals. Excipients which can be used include organic or inorganic substances which are suitable for enteral (for example oral) or parenteral administration or topical application and which do not react with the new compounds, for example water, vegetable oils, benzyl alcohols, polyethylene glycols, gelatine, carbohydrates, such as lactose or starch, magnesium stearate, talc and white petroleum jelly. Formulations used for enteral administration are, in particular, tablets, dragees, capsules, syrups, elixirs, drops or suppositories; for parenteral administration are solutions, preferably oily or aqueous solutions, and also suspensions, emulsions or implants; and for topical application are ointments, creams or powders. The new compounds can also be lyophilized and the resulting lyophilizates can be used, for example, to prepare injection preparations. The indicated formulations can be sterilized and/or contain auxiliaries, such as lubricants, preservatives, stabilizing agents and/or wetting agents, emulsifiers, salts for influencing the osmotic pressure, buffer substances, dyestuffs, flavorings and/or aroma substances. They can, if desired, also contain one or more further active ingredients, for example, one or more vitamins.

The invention also relates to the use of the compounds of the formula I and their physiologically acceptable acid addition salts in combating illnesses, especially depressions of diverse aetiology and symptomatology, and also to their use in the therapeutic treatment of the human or animal body.

As a rule, the substances according to the invention are administered analogously to known psychopharmaceuticals available commercially (for example imipramine), preferably in dosages of between 2 and 500 mg and especially of between 10 and 50 mg per dosage unit. The daily dose is preferably between about 0.05 and 10 mg/kg of body weight. The particular does for each specific patient depends, however, on very diverse factors, for example, on the effectiveness of the particular compound used; on the age, body weight, general state of health, sex, diet and rate of excretion of the patient; on the time and route of administration; on the combination of medicaments; and on the severity of the particular disorder for which therapy is being given. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperature are set forth uncorrected in degrees Celsius; unless otherwise indicated, all parts and percentages are by weight.

Each of the compounds of formula I named in the examples which follow is particularly suitable for the preparation of pharmaceutical formulations.

In the examples which follow, "customary working up" signifies:

Water is added if necessary and the mixture is extracted with an organic solvent, such as benzene, chloroform or methylene chloride, the organic phase is separated off, dried over sodium sulfate and filtered, the filtrate is evaporated and the residue is purified by chromatography and/or crystallization.

The Rf values were obtained on silica gel using toluene/triethylamine (8:2) unless stated otherwise.

EXAMPLE 1

5.1 g of p-chlorophenol are dissolved in 20 ml of absolute ethanol, 60 ml of 0.5 N ethanolic KOH are added and the mixture is stirred for one hour at 20°. The reaction mixture is evaporated and the residue is taken up in 100 ml of absolute DMF. 1.62 g of 1-methyl-2-(2-chloroethyl)-piperidine are added, the mixture is boiled for 4 hours and is then again evaporated, the residue is worked up in the customary manner and this gives 1-methyl-2-(2-p-chlorophenoxyethyl)-piperidine. Hydrochloride, m.p. 139-140.

EXAMPLES 2 to 451

The following compounds are obtained analogously to Example 1 from the corresponding phenols of formula II and 2-(2-chloroethyl)-pyrrolidine, 1-methyl-2-(2-chloroethyl)-pyrrolidine, 2-(2-chloro-2-phenylethyl)-pyrrolidine, 1-methyl-2-(2-chloro-2-phenylethyl)-pyrrolidine, 2-(2-chloroethyl)-piperidine, 1-methyl-2-(2-chloroethyl)-piperidine, 2-(2-chloro-2-phenylethyl)-piperidine, 1-methyl-2-(2-chloro-2-phenylethyl)-piperidine, 3-methyl-4-chloro-hexahydroazepine, 1,3-dimethyl-4-chloro-hexahydroazepine or the corresponding bromine compounds:

2. 2-(2-Phenoxyethyl)-pyrrolidine.
3. 2-(2-o-Fluorophenoxyethyl)-pyrrolidine.
4. 2-(2-m-Fluorophenoxyethyl)-pyrrolidine.
5. 2-(2-p-Fluorophenoxyethyl)-pyrrolidine.
6. 2-(2-o-Chlorophenoxyethyl)-pyrrolidine.
7. 2-(2-m-Chlorophenoxyethyl)-pyrrolidine.
8. 2-(2-p-Chlorophenoxyethyl)-pyrrolidine.
9. 2-(2-o-Bromophenoxyethyl)-pyrrolidine.
10. 2-(2-m-Bromophenoxyethyl)-pyrrolidine.
11. 2-(2-p-Bromophenoxyethyl)-pyrrolidine.
12. 2-(2-o-Tolyloxyethyl)-pyrrolidine.
13. 2-(2-m-Tolyloxyethyl)-pyrrolidine.
14. 2-(2-p-Tolyloxyethyl)-pyrrolidine.
15. 2-(2-o-Methoxyphenoxyethyl)-pyrrolidine.
16. 2-(2-m-Methoxyphenoxyethyl)-pyrrolidine.
17. 2-(2-p-Methoxyphenoxyethyl)-pyrrolidine.
18. 2-(2-o-Cyclopentyloxyphenoxyethyl)-pyrrolidine.
19. 2-(2-m-Cyclopentyloxyphenoxyethyl)-pyrrolidine.
20. 2-(2-p-Cyclopentyloxyphenoxyethyl)-pyrrolidine.
21. 2-(2-o-Cyclohexyloxyphenoxyethyl)-pyrrolidine.
22. 2-(2-m-Cyclohexyloxyphenoxyethyl)-pyrrolidine.
23. 2-(2-p-Cyclohexyloxyphenoxyethyl)-pyrrolidine.
24. 2-(2-o-Trifluoromethylphenoxyethyl)-pyrrolidine.
25. 2-(2-m-Trifluoromethylphenoxyethyl)-pyrrolidine.
26. 2-(2-p-Trifluoromethylphenoxyethyl)-pyrrolidine.
27. 2-(2-o-Cyanophenoxyethyl)-pyrrolidine.
28. 2-(2-m-Cyanophenoxyethyl)-pyrrolidine.
29. 2-(2-p-Cyanophenoxyethyl)-pyrrolidine.
30. 2-(2-o-Methylthiophenoxyethyl)-pyrrolidine.
31. 2-(2-m-Methylthiophenoxyethyl)-pyrrolidine.
32. 2-(2-p-Methylthiophenoxyethyl)-pyrrolidine.
33. 2-(2-o-Trifluoromethylthiophenoxyethyl)-pyrrolidine.
34. 2-(2-m-Trifluoromethylthiophenoxyethyl)-pyrrolidine.
35. 2-(2-p-Trifluoromethylthiophenoxyethyl)-pyrrolidine.
36. 2-(2-o-Hydroxyphenoxyethyl)-pyrrolidine.
37. 2-(2-m-Hydroxyphenoxyethyl)-pyrrolidine.
38. 2-(2-p-Hydroxyphenoxyethyl)-pyrrolidine.
39. 2-(2-o-Acetoxyphenoxyethyl)-pyrrolidine.
40. 2-(2-m-Acetoxyphenoxyethyl)-pyrrolidine.
41. 2-(2-p-Acetoxyphenoxyethyl)-pyrrolidine.
42. 2-(2-p-Propionyloxyphenoxyethyl)-pyrrolidine.
43. 2-(2-p-Butyryloxyphenoxyethyl)-pyrrolidine.
44. 2-(2-p-Valeryloxyphenoxyethyl)-pyrrolidine.
45. 2-(2-p-Hexanoyloxyphenoxyethyl)-pyrrolidine.
46. 2-(2-p-Heptanoyloxyphenoxyetnyl)-pyrrolidine.
47. 2-[2-(3,4-Dimethoxyphenoxy)-ethyl]-pyrrolidine.
48. 2-[2-(2-Methoxy-5-trifluoromethylphenoxy)-ethyl]-pyrrolidine.
49. 2-[2-(2-Hydroxy-4-chlorophenoxy)-ethyl]-pyrrolidine.
50. 2-[2-(2-Heptanoyloxy-4-chlorophenoxy)-ethyl]-pyrrolidine.
51. 2-[2-(2-Decanoyloxy-4-chlorophenoxy)-ethyl]-pyrrolidine.
52. 1-Methyl-2-(2-phenoxyethyl)-pyrrolidine.
53. 1-Methyl-2-(2-o-fluorophenoxyethyl)-pyrrolidine.
54. 1-Methyl-2-(2-m-fluorophenoxyethyl)-pyrrolidine.
55. 1-Methyl-2-(2-p-fluorophenoxyethyl)-pyrrolidine, oil, Rf 0.77 (CHCl$_3$/triethylamine, 8:2).
56. 1-Methyl-2-(2-o-chlorophenoxyethyl)-pyrrolidine.
57. 1-Methyl-2-(2-m-chlorophenoxyethyl)-pyrrolidine.
58. 1-Methyl-2-(2-p-chlorophenoxyethyl)-pyrrolidine, hydrobromide, m.p. 137°–140°.
59. 1-Methyl-2-(2-o-bromophenoxyethyl)-pyrrolidine.
60. 1-Methyl-2-(2-m-bromophenoxyethyl)-pyrrolidine.
61. 1-Methyl-2-(2-p-bromophenoxyethyl)-pyrrolidine.
62. 1-Methyl-2-(2-o-tolyloxyethyl)-pyrrolidine.
63. 1-Methyl-2-(2-m-tolyloxyethyl)-pyrrolidine.
64. 1-Methyl-2-(2-p-tolyloxyethyl)-pyrrolidine.
65. 1-Methyl-2-(2-p-ethylphenoxyethyl)-pyrrolidine.
66. 1-Methyl-2-(2-p-n-butylphenoxyethyl)-pyrrolidine.
67. 1-Methyl-2-(2-o-methoxyphenoxyethyl)-pyrrolidine, b.p. 106°–108.5°/0.09 mm.
68. 1-Methyl-2-(2-m-methoxyphenoxyethyl)-pyrrolidine.
69. 1-Methyl-2-(2-p-methoxyphenoxyethyl)-pyrrolidine.
70. 1-Methyl-2-(2-p-ethoxyphenoxyethyl)-pyrrolidine.
71. 1-Methyl-2-(2-p-n-butoxyphenoxyethyl)-pyrrolidine.
72. 1-Methyl-2-(2-p-cyclopropyloxyphenoxyethyl)-pyrrolidine.
73. 1-Methyl-2-(2-o-cyclopentyloxyphenoxyethyl)-pyrrolidine.
74. 1-Methyl-2-(2-m-cyclopentyloxyphenoxyethyl)-pyrrolidine.
75. 1-Methyl-2-(2-p-cyclopentyloxyphenoxyethyl)-pyrrolidine.
76. 1-Methyl-2-(2-o-cyclohexyloxyphenoxyethyl)-pyrrolidine.
77. 1-Methyl-2-(2-m-cyclohexyloxyphenoxyethyl)-pyrrolidine.
78. 1-Methyl-2-(2-p-cyclohexyloxyphenoxyethyl)-pyrrolidine.
79. 1-Methyl-2-(2-o-trifluoromethylphenoxyethyl)-pyrrolidine, hydrobromide, m.p. 113°–115°.
80. 1-Methyl-2-(2-m-trifluoromethylphenoxyethyl)-pyrrolidine.
81. 1-Methyl-2-(2-p-trifluoromethylphenoxyethyl)-pyrrolidine.
82. 1-Methyl-2-(2-o-cyanophenoxyethyl)-pyrrolidine.
83. 1-Methyl-2-(2-m-cyanophenoxyethyl)-pyrrolidine.
84. 1-Methyl-2-(2-p-cyanophenoxyethyl)-pyrrolidine.
85. 1-Methyl-2-(2-o-methylthiophenoxyethyl)-pyrrolidine.
86. 1-Methyl-2-(2-m-methylthiophenoxyethyl)-pyrrolidine.
87. 1-Methyl-2-(2-p-methylthiophenoxyethyl)-pyrrolidine.
88. 1-Methyl-2-(2-p-ethylthiophenoxyethyl)-pyrrolidine.
89. 1-Methyl-2-(2-p-n-butylthiophenoxyethyl)-pyrrolidine.
90. 1-Methyl-2-(2-o-trifluoromethylthiophenoxyethyl)-pyrrolidine.
91. 1-Methyl-2-(2-m-trifluoromethylthiophenoxyethyl)-pyrrolidine.
92. 1-Methyl-2-(2-p-trifluoromethylthiophenoxyethyl)-pyrrolidine.
93. 1-Methyl-2-(2-o-hydroxyphenoxyethyl)-pyrrolidine.
94. 1-Methyl-2-(2-m-hydroxyphenoxyethyl)-pyrrolidine.
95. 1-Methyl-2-(2-p-hydroxyphenoxyethyl)-pyrrolidine.

96. 1-Methyl-2-(2-o-acetoxyphenoxyethyl)-pyrrolidine.
97. 1-Methyl-2-(2-m-acetoxyphenoxyethyl)-pyrrolidine.
98. 1-Methyl-2-(2-p-acetoxyphenoxyethyl)-pyrrolidine.
99. 1-Methyl-2-(2-p-propionyloxyphenoxyethyl)-pyrrolidine.
100. 1-Methyl-2-(2-p-butyryloxyphenoxyethyl)-pyrrolidine.
101. 1-Methyl-2-(2-p-valeryloxyphenoxyethyl)-pyrrolidine.
102. 1-Methyl-2-(2-p-hexanoyloxyphenoxyethyl)-pyrrolidine.
103. 1-Methyl-2-(2-p-heptanoyloxyphenoxyethyl)-pyrrolidine.
104. 1-Methyl-2-[2-(3,4-dimethoxyphenoxy)-ethyl]-pyrrolidine.
105. 1-Methyl-2-[2-(2-methoxy-5-trifluoromethylphenoxy)-ethyl]-pyrrolidine.
106. 1-Methyl-2-[2-(2-hydroxy-4-chlorophenoxy)-ethyl]-pyrrolidine.
107. 1-Methyl-2-[2-(2-heptanoyloxy-4-chlorophenoxy)-ethyl]-pyrrolidine.
108. 1-Methyl-2-[2-(2-decanoyloxy-4-chlorophenoxy)-ethyl]-pyrrolidine.
109. 2-(2-Phenoxy-2-phenyl-ethyl)pyrrolidine.
110. 2-(2-p-Fluorophenoxy-2-phenyl-ethyl)pyrrolidine.
111. 2-(2-o-Chlorophenoxy-2-phenyl-ethyl)-pyrrolidine.
112. 2-(2-m-Chlorophenoxy-2-phenyl-ethyl)-pyrrolidine.
113. 2-(2-p-Chlorophenoxy-2-phenyl-ethyl)-pyrrolidine.
114. 2-(2-o-Methoxyphenoxy-2-phenyl-ethyl)-pyrrolidine.
115. 2-(2-p-Methoxyphenoxy-2-phenyl-ethyl)-pyrrolidine.
116. 2-(2-m-Trifluoromethylphenoxy-2-phenyl-ethyl)-pyrrolidine.
117. 2-(2-p-Trifluoromethylphenoxy-2-phenyl-ethyl)-pyrrolidine.
118. 2-(2-o-Methylthiophenoxy-2-phenyl-ethyl)-pyrrolidine.
119. 2-(2-p-Methylthiophenoxy-2-phenyl-ethyl)-pyrrolidine.
120. 2-(2-p-Trifluoromethylthiophenoxy-2-phenyl-ethyl)-pyrrolidine.
121. 1-Methyl-2-(2-phenoxy-2-phenyl-ethyl)-pyrrolidine.
122. 1-Methyl-2-(2-p-fluorophenoxy-2-phenyl-ethyl)-pyrrolidine.
123. 1-Methyl-2-(2-o-chlorophenoxy-2-phenyl-ethyl)-pyrrolidine.
124. 1-Methyl-2-(2-m-chlorophenoxy-2-phenyl-ethyl)-pyrrolidine.
125. 1-Methyl-2-(2-p-chlorophenoxy-2-phenyl-ethyl)-pyrrolidine.
126. 1-Methyl-2-(2-o-methoxyphenoxy-2-phenyl-ethyl)-pyrrolidine.
127. 1-Methyl-2-(2-p-methoxyphenoxy-2-phenyl-ethyl)-pyrrolidine.
128. 1-Methyl-2-(2-m-trifluoromethylphenoxy-2-phenyl-ethyl)-pyrrolidine.
129. 1-Methyl-2-(2-p-trifluoromethylphenoxy-2-phenyl-ethyl)-pyrrolidine.
130. 1-Methyl-2-(2-o-methylthiophenoxy-2-phenyl-ethyl)-pyrrolidine.
131. 1-Methyl-2-(2-p-methylthiophenoxy-2-phenyl-ethyl)-pyrrolidine.
132. 1-Methyl-2-(2-p-trifluoromethylthiophenoxy-2-phenyl-ethyl)-pyrrolidine.
133. 2-(2-Phenoxyethyl)-piperidine.
134. 2-(2-o-Fluorophenoxyethyl)-piperidine.
135. 2-(2-m-Fluorophenoxyethyl)-piperidine.
136. 2-(2-p-Fluorophenoxyethyl)-piperidine, hydrochloride, m.p. 158°–160°.
137. 2-(2-o-Chlorophenoxyethyl)-piperidine.
138. 2-(2-m-Chlorophenoxyethyl)-piperidine.
139. 2-(2-p-Chlorophenoxyethyl)-piperidine, hydrochloride, m.p. 220°.
140. 2-(2-o-Bromophenoxyethyl)-piperidine.
141. 2-(2-m-Bromophenoxyethyl)-piperidine.
142. 2-(2-p-Bromophenoxyethyl)-piperidine.
143. 2-(2-o-Tolyloxyethyl)-piperidine.
144. 2-(2-m-Tolyloxyethyl)-piperidine.
145. 2-(2-p-Tolyloxyethyl)-piperidine.
146. 2-(2-o-Methoxyphenoxyethyl)-piperidine.
147. 2-(2-m-Methoxyphenoxyethyl)-piperidine.
148. 2-(2-p-Methoxyphenoxyethyl)-piperidine, hydrochloride, m.p. 138°–140°.
149. 2-(2-o-Cyclopentyloxyphenoxyethyl)-piperidine.
150. 2-(2-m-Cyclopentyloxyphenoxyethyl)-piperidine.
151. 2-(2-p-Cyclopentyloxyphenoxyethyl)-piperidine.
152. 2-(2-o-Cyclohexyloxyphenoxyethyl)-piperidine.
153. 2-(2-m-Cyclohexyloxyphenoxyethyl)-piperidine.
154. 2-(2-p-Cyclohexyloxyphenoxyethyl)-piperidine.
155. 2-(2-o-Trifluoromethylphenoxyethyl)-piperidine.
156. 2-(2-m-Trifluoromethylphenoxyethyl)-piperidine, hydrochloride, m.p. 152°–153°.
157. 2-(2-p-Trifluoromethylphenoxyethyl)-piperidine.
158. 2-(2-o-Cyanophenoxyethyl)-piperidine.
159. 2-(2-m-Cyanophenoxyethyl)-piperidine.
160. 2-(2-p-Cyanophenoxyethyl)-piperidine.
161. 2-(2-o-Methylthiophenoxyethyl)-piperidine.
162. 2-(2-m-Methylthiophenoxyethyl)-piperidine.
163. 2-(2-p-Methylthiophenoxyethyl)-piperidine, m.p. 65°–67°.
164. 2-(2-o-Trifluoromethylthiophenoxyethyl)-piperidine.
165. 2-(2-m-Trifluoromethylthiophenoxyethyl)-piperidine.
166. 2-(2-p-Trifluoromethylthiophenoxyethyl)-piperidine.
167. 2-(2-o-Hydroxyphenoxyethyl)-piperidine.
168. 2-(2-m-Hydroxyphenoxyethyl)-piperidine.
169. 2-(2-p-Hydroxyphenoxyethyl)-piperidine.
170. 2-(2-o-Acetoxyphenoxyethyl)-piperidine.
171. 2-(2-m-Acetoxyphenoxyethyl)-piperidine.
172. 2-(2-p-Acetoxyphenoxyethyl)-piperidine.
173. 2-(2-p-Propionyloxyphenoxyethyl)-piperidine.
174. 2-(2-p-Butyryloxyphenoxyethyl)-piperidine.
175. 2-(2-p-Valeryloxyphenoxyethyl)-piperidine.
176. 2-(2-p-Hexanoyloxyphenoxyethyl)-piperidine.
177. 2-(2-p-Heptanoyloxyphenoxyethyl)-piperidine.
178. 2-[2-(3,4-Dimethoxyphenoxy)-ethyl]-piperidine.
179. 2-[2-(2-Methoxy-5-trifluoromethylphenoxy)-ethyl]-piperidine.
180. 2-[2-(2-Hydroxy-4-chlorophenoxy)-ethyl]-piperidine.
181. 2-[2-(2-Heptanoyloxy-4-chlorophenoxy)-ethyl]-piperidine.
182. 2-[2-(2-Decanoyloxy-4-chlorophenoxy)-ethyl]-piperidine.
183. 1-Methyl-2-(2-phenoxyethyl)-piperidine, hydrochloride, m.p. 122°–124°.
184. 1-Methyl-2-(2-o-fluorophenoxyethyl)-piperidine.
185. 1-Methyl-2-(2-m-fluorophenoxyethyl)-piperidine.

186. 1-Methyl-2-(2-o-chlorophenoxyethyl)-piperidine, hydrochloride, m.p. 146°–148°.
187. 1-Methyl-2-(2-m-chlorophenoxyethyl)-piperidine.
188. 1-Methyl-2-(2-o-bromophenoxyethyl)-piperidine.
189. 1-Methyl-2-(2-m-bromophenoxyethyl)-piperidine.
190. 1-Methyl-2-(2-p-bromophenoxyethyl)-piperidine.
191. 1-Methyl-2-(2-o-tolyloxyethyl)-piperidine.
192. 1-Methyl-2-(2-m-tolyloxyethyl)-piperidine.
193. 1-Methyl-2-(2-p-tolyloxyethyl)-piperidine, hydrochloride, m.p. 138°–139°.
194. 1-Methyl-2-(2-p-ethylphenoxyethyl)-piperidine.
195. 1-Methyl-2-(2-p-n-butylphenoxyethyl)-piperidine.
196. 1-Methyl-2-(2-o-methoxyphenoxyethyl)-piperidine.
197. 1-Methyl-2-(2m-methoxyphenoxyethyl)-piperidine.
198. 1-Methyl-2-(2-p-methoxyphenoxyethyl)-piperidine.
199. 1-Methyl-2-(2-p-ethoxyphenoxyethyl)-piperidine.
200. 1-Methyl-2-(2-p-n-butoxyphenoxyethyl)-piperidine.
201. 1-Methyl-2-(2-p-cyclopropyloxyphenoxyethyl)-piperidine.
202. 1-Methyl-2-(2-o-cyclopentyloxyphenoxyethyl)-piperidine.
203. 1-Methyl-2-(2-m-cyclopentyloxyphenoxyethyl)-piperidine.
204. 1-Methyl-2-(2-p-cyclopentyloxyphenoxyethyl)-piperidine.
205. 1-Methyl-2-(2-o-cyclohexyloxyphenoxyethyl)-piperidine.
206. 1-Methyl-2-(2-m-cyclohexyloxyphenoxyethyl)-piperidine.
207. 1-Methyl-2-(2-p-cyclohexyloxyphenoxyethyl)-piperidine.
208. 1-Methyl-2-(2-o-trifluoromethylphenoxyethyl)-piperidine.
209. 1-Methyl-2-(2-m-trifluoromethylphenoxyethyl)-piperidine, hydrochloride monohydrate, m.p. 42°–43°.
210. 1-Methyl-2-(2-p-trifluoromethylphenoxyethyl)-piperidine, hydrochloride, m.p. 138°–139°.
211. 1-Methyl-2-(2-o-cyanophenoxyethyl)-piperidine.
212. 1-Methyl-2-(2-m-cyanophenoxyethyl)-piperidine.
213. 1-Methyl-2-(2-p-cyanophenoxyethyl)-piperidine.
214. 1-Methyl-2-(2-o-methylthiophenoxyethyl)-piperidine.
215. 1-Methyl-2-(2-m-methylthiophenoxyethyl)-piperidine.
216. 1-Methyl-2-(2-p-methylthiophenoxyethyl)-piperidine, hydrochloride, m.p. 143°–144°.
217. 1-Methyl-2-(2-p-ethylthiophenoxyethyl)-piperidine.
218. 1-Methyl-2-(2-p-n-butylthiophenoxyethyl)-piperidine.
219. 1-Methyl-2-(2-o-trifluoromethylthiophenoxyethyl)-piperidine.
220. 1-Methyl-2-(2-m-trifluoromethylthiophenoxyethyl)-piperidine.
221. 1-Methyl-2-(2-p-trifluoromethylthiophenoxyethyl)-piperidine.
222. 1-Methyl-2-(2-o-hydroxyphenoxyethyl)-piperidine.
223. 1-Methyl-2-(2-m-hydroxyphenoxyethyl)-piperidine.
224. 1-Methyl-2-(2-p-hydroxyphenoxyethyl)-piperidine, hydrochloride, m.p. 182°.
225. 1-Methyl-2-(2-o-acetoxyphenoxyethyl)-piperidine.
226. 1-Methyl-2-(2-m-acetoxyphenoxyethyl)-piperidine.
227. 1-Methyl-2-(2-p-acetoxyphenoxyethyl)-piperidine.
228. 1-Methyl-2-(2-p-propionyloxyphenoxyethyl)-piperidine.
229. 1-Methyl-2-(2-p-butyryloxyphenoxyethyl)-piperidine.
230. 1-Methyl-2-(2-p-valeryloxyphenoxyethyl)-piperidine.
231. 1-Methyl-2-(2-p-hexanoyloxyphenoxyethyl)-piperidine.
232. 1-Methyl-2-(2-p-heptanoyloxyphenoxyethyl)-piperidine.
233. 1-Methyl-2-[2-(3,4-dimethoxyphenoxy)-ethyl]-piperidine, hydrochloride, m.p. 176°–177°.
234. 1-Methyl-2-[2-(2-methoxy-5-trifluoromethylphenoxy)-ethyl]-piperidine.
235. 1-Methyl-2-[2-(2-hydroxy-4-chlorophenoxy)-ethyl]-piperidine.
236. 1-Methyl-2-[2-(2-heptanoyloxy-4-chlorophenoxy)-ethyl]-piperidine.
237. 1-Methyl-2-[2-(2-decanoyloxy-4-chlorophenoxy)-ethyl]-piperidine.
238. 2-(2-Phenoxy-2-phenyl-ethyl)-piperidine.
239. 2-(2-o-Fluorophenoxy-2-phenyl-ethyl)-piperidine.
240. 2-(2-m-Fluorophenoxy-2-phenyl-ethyl)-piperidine.
241. 2-(2-p-Fluorophenoxy-2-phenyl-ethyl)-piperidine.
242. 2-(2-o-Chlorophenoxy-2-phenyl-ethyl)-piperidine.
243. 2-(2-m-Chlorophenoxy-2-phenyl-ethyl)-piperidine.
244. 2-(2-p-Chlorophenoxy-2-phenyl-ethyl)-piperidine.
245. 2-(2-o-Bromophenoxy-2-phenyl-ethyl)-piperidine.
246. 2-(2-m-Bromophenoxy-2-phenyl-ethyl)-piperidine.
247. 2-(2-p-Bromophenoxy-2-phenyl-ethyl)-piperidine.
248. 2-(2-o-Tolyloxy-2-phenyl-ethyl)-piperidine.
249. 2-(2-m-Tolyloxy-2-phenyl-ethyl)-piperidine.
250. 2-(2-p-Tolyloxy-2-phenyl-ethyl)-piperidine.
251. 2-(2-o-Methoxyphenoxy-2-phenyl-ethyl)-piperidine.
252. 2-(2-m-Methoxyphenoxy-2-phenyl-ethyl)-piperidine.
253. 2-(2-p-Methoxyphenoxy-2-phenyl-ethyl)-piperidine.
254. 2-(2-o-Cyclopentyloxy-2-phenyl-ethyl)-piperidine.
255. 2-(2-m-Cyclopentyloxy-2-phenyl-ethyl)-piperidine.
256. 2-(2-p-Cyclopentyloxy-2-phenyl-ethyl)-piperidine.
257. 2-(2-o-Cyclohexyloxy-2-phenyl-ethyl)-piperidine.
258. 2-(2-m-Cyclohexyloxy-2-phenyl-ethyl)-piperidine.
259. 2-(2-p-Cyclohexyloxy-2-phenyl-ethyl)-piperidine.
260. 2-(2-o-Trifluoromethylphenoxy-2-phenyl-ethyl)-piperidine.
261. 2-(2-m-Trifluoromethylphenoxy-2-phenyl-ethyl)-piperidine.
262. 2-(2-p-Trifluoromethylphenoxy-2-phenyl-ethyl)-piperidine.
263. 2-(2-o-Cyanophenoxy-2-phenyl-ethyl)-piperidine.
264. 2-(2-m-Cyanophenoxy-2-phenyl-ethyl)-piperidine.
265. 2-(2-p-Cyanophenoxy-2-phenyl-ethyl)-piperidine.
266. 2-(2-o-Methylthiophenoxy-2-phenyl-ethyl)-piperidine.
267. 2-(2-m-Methylthiophenoxy-2-phenyl-ethyl)-piperidine.
268. 2-(2-p-Methylthiophenoxy-2-phenyl-ethyl)-piperidine.
269. 2-(2-o-Trifluoromethylthiophenoxy-2-phenyl-ethyl)-piperidine.
270. 2-(2-m-Trifluoromethylthiophenoxy-2-phenyl-ethyl)-piperidine.
271. 2-(2-p-Trifluoromethylthiophenoxy-2-phenyl-ethyl)-piperidine.

272. 2-(2-o-Hydroxyphenoxy-2-phenyl-ethyl)-piperidine.
273. 2-(2-m-Hydroxyphenoxy-2-phenyl-ethyl)-piperidine.
274. 2-(2-p-Hydroxyphenoxy-2-phenyl-ethyl)-piperidine.
275. 2-(2-o-Acetoxyphenoxy-2-phenyl-ethyl)-piperidine.
276. 2-(2-m-Acetoxyphenoxy-2-phenyl-ethyl)-piperidine.
277. 2-(2-p-Acetoxyphenoxy-2-phenyl-ethyl)-piperidine.
278. 2-(2-p-Propionyloxyphenoxy-2-phenyl-ethyl)-piperidine.
279. 2-(2-p-Butyryloxyphenoxy-2-phenyl-ethyl)-piperidine.
280. 2-(2-p-Valeryloxyphenoxy-2-phenyl-ethyl)-piperidine.
281. 2-(2-p-Hexanoyloxyphenoxy-2-phenyl-ethyl)-piperidine.
282. 2-(2-p-Heptanoyloxyphenoxy-2-phenyl-ethyl)-piperidine.
283. 2-[2-(3,4-Dimethoxyphenoxy)-2-phenyl-ethyl]-piperidine.
284. 2-[2-(2-Methoxy-5-trifluoromethyl-phenoxy)-2-phenyl-ethyl]-piperidine.
285. 2-[2-(2-Hydroxy-4-chlorophenoxy)-2-phenyl-ethyl]-piperidine.
286. 2-[2-(2-Heptanoyloxy-4-chlorophenoxy)-2-phenyl-ethyl]-piperidine.
287. 2-[2-(2-Decanoyloxy-4-chlorophenoxy)-2-phenyl-ethyl]-piperidine.
288. 1-Methyl-2-(2-phenoxy-2-phenyl-ethyl)-piperidine.
289. 1-Methyl-2-(2-o-fluorophenoxy-2-phenyl-ethyl)-piperidine.
290. 1-Methyl-2-(2-m-fluorophenoxy-2-phenyl-ethyl)-piperidine.
291. 1-Methyl-2-(2-p-fluorophenoxy-2-phenyl-ethyl)-piperidine, hydrochloride, m.p. 85°–86°.
292. 1-Methyl-2-(2-o-chlorophenoxy-2-phenyl-ethyl)-piperidine.
293. 1-Methyl-2-(2-m-chlorophenoxy-2-phenyl-ethyl)-piperidine.
294. 1-Methyl-2-(2-p-chlorophenoxy-2-phenyl-ethyl)-piperidine, hydrochloride, m.p. 88°.
295. 1-Methyl-2-(2-o-bromophenoxy-2-phenyl-ethyl)-piperidine.
296. 1-Methyl-2-(2-m-bromophenoxy-2-phenyl-ethyl)-piperidine.
297. 1-Methyl-2-(2-p-bromophenoxy-2-phenyl-ethyl)-piperidine.
298. 1-Methyl-2-(2-o-tolyloxy-2-phenyl-ethyl)-piperidine.
299. 1-Methyl-2-(2-m-tolyloxy-2-phenyl-ethyl)-piperidine.
300. 1-Methyl-2-(2-p-tolyloxy-2-phenyl-ethyl)-piperidine, hydrochloride, m.p. 183°.
301. 1-Methyl-2-(2-o-methoxyphenoxy-2-phenyl-ethyl)-piperidine, hydrochloride, m.p. 158°.
302. 1-Methyl-2-(2-m-methoxyphenoxy-2-phenyl-ethyl)-piperidine.
303. 1-Methyl-2-(2-p-methoxyphenoxy-2-phenyl-ethyl)-piperidine, hydrochloride, m.p. 188°.
304. 1-Methyl-2-(2-o-cyclopentyloxy-2-phenyl-ethyl)-piperidine.
305. 1-Methyl-2-(2-m-cyclopentyloxy-2-phenyl-ethyl)-piperidine.
306. 1-Methyl-2-(2-p-cyclopentyloxy-2-phenyl-ethyl)-piperidine.
307. 1-Methyl-2-(2-o-cyclohexyloxy-2-phenyl-ethyl)-piperidine.
308. 1-Methyl-2-(2-m-cyclohexyloxy-2-phenyl-ethyl)-piperidine.
309. 1-Methyl-2-(2-p-cyclohexyloxy-2-phenyl-ethyl)-piperidine.
310. 1-Methyl-2-(2-o-trifluoromethylphenoxy-2-phenyl-ethyl)-piperidine.
311. 1-Methyl-2-(2-m-trifluoromethylphenoxy-2-phenyl-ethyl)-piperidine.
312. 1-Methyl-2-(2-p-trifluoromethylphenoxy-2-phenyl-ethyl)-piperidine, hydrochloride, m.p. 135°.
313. 1-Methyl-2-(2-o-cyanophenoxy-2-phenyl-ethyl)-piperidine.
314. 1-Methyl-2-(2-m-cyanophenoxy-2-phenyl-ethyl)-piperidine.
315. 1-Methyl-2-(2-p-cyanophenoxy-2-phenyl-ethyl)-piperidine.
316. 1-Methyl-2-(2-o-methylthiophenoxy-2-phenyl-ethyl)-piperidine, hydrochloride, m.p. 164°.
317. 1-Methyl-2-(2-m-methylthiophenoxy-2-phenyl-ethyl)-piperidine.
318. 1-Methyl-2-(2-p-methylthiophenoxy-2-phenyl-ethyl)-piperidine, hydrochloride, m.p. 195°–196°.
319. 1-Methyl-2-(2-o-trifluoromethylthiophenoxy-2-phenyl-ethyl)-piperidine.
320. 1-Methyl-2-(2-m-trifluoromethylthiophenoxy-2-phenyl-ethyl)-piperidine.
321. 1-Methyl-2-(2-p-trifluoromethylthiophenoxy-2-phenyl-ethyl)-piperidine.
322. 1-Methyl-2-(2-o-hydroxyphenoxy-2-phenyl-ethyl)-piperidine.
323. 1-Methyl-2-(2-m-hydroxyphenoxy-2-phenyl-ethyl)-piperidine.
324. 1-Methyl-2-(2-p-hydroxyphenoxy-2-phenyl-ethyl)-piperidine.
325. 1-Methyl-2-(2-o-acetoxyphenoxy-2-phenyl-ethyl)-piperidine.
326. 1-Methyl-2-(2-m-acetoxyphenoxy-2-phenyl-ethyl)-piperidine.
327. 1-Methyl-2-(2-p-acetoxyphenoxy-2-phenyl-ethyl)-piperidine.
328. 1-Methyl-2-(2-p-propionyloxyphenoxy-2-phenyl-ethyl)-piperidine.
329. 1-Methyl-2-(2-p-butyryloxyphenoxy-2-phenyl-ethyl)-piperidine.
330. 1-Methyl-2-(2-p-valeryloxyphenoxy-2-phenyl-ethyl)-piperidine.
331. 1-Methyl-2-(2-p-hexanoyloxyphenoxy-2-phenyl-ethyl)-piperidine.
332. 1-Methyl-2-(2-p-heptanoyloxyphenoxy-2-phenyl-ethyl)-piperidine.
333. 1-Methyl-2-[2-(3,4-dimethoxyphenoxy)-2-phenyl-ethyl]-piperidine.
334. 1-Methyl-2-[2-(2-methoxy-5-trifluoromethylphenoxy)-2-phenyl-ethyl]-piperidine.
335. 1-Methyl-2-[2-(2-hydroxy-4-chlorophenoxy)-2-phenyl-ethyl]-piperidine.
336. 1-Methyl-2-[2-(2-heptanoyloxy-4-chlorophenoxy)-2-phenyl-ethyl]-piperidine.
337. 1-Methyl-2-[2-(2-decanoyloxy-4-chlorophenoxy)-2-phenyl-ethyl]-piperidine.
338. 3-Methyl-4-phenoxy-hexahydroazepine.
339. 3-Methyl-4-o-fluorophenoxy-hexahydroazepine.
340. 3-Methyl-4-m-fluorophenoxy-hexahydroazepine.
341. 3-Methyl-4-p-fluorophenoxy-hexahydroazepine.

342. 3-Methyl-4-o-chlorophenoxy-hexahydroazepine.
343. 3-Methyl-4-m-chlorophenoxy-hexahydroazepine.
344. 3-Methyl-4-p-chlorophenoxy-hexahydroazepine.
345. 3-Methyl-4-o-bromophenoxy-hexahydroazepine.
346. 3-Methyl-4-m-bromophenoxy-hexahydroazepine.
347. 3-Methyl-4-p-bromophenoxy-hexahydroazepine.
348. 3-Methyl-4-o-tolyloxy-hexahydroazepine.
349. 3-Methyl-4-m-tolyloxy-hexahydroazepine.
350. 3-Methyl-4-p-tolyloxy-hexahydroazepine.
351. 3-Methyl-4-p-ethylphenoxy-hexahydroazepine.
352. 3-Methyl-4-p-isobutylphenoxy-hexahydroazepine.
353. 3-Methyl-4-o-methoxyphenoxy-hexahydroazepine.
354. 3-Methyl-4-m-methoxyphenoxy-hexahydroazepine.
355. 3-Methyl-4-p-methoxyphenoxy-hexahydroazepine.
356. 3-Methyl-4-p-ethoxyphenoxy-hexahydroazepine.
357. 3-Methyl-4-p-sec.-butoxyphenoxy-hexahydroazepine.
358. 3-Methyl-4-p-cyclopropyloxyphenoxy-hexahydroazepine.
359. 3-Methyl-4-o-cyclopentyloxyphenoxy-hexahydroazepine.
360. 3-Methyl-4-m-cyclopentyloxyphenoxy-hexahydroazepine.
361. 3-Methyl-4-p-cyclopentyloxyphenoxy-hexahydroazepine.
362. 3-Methyl-4-o-cyclohexyloxyphenoxy-hexahydroazepine.
363. 3-Methyl-4-m-cyclohexyloxyphenoxy-hexahydroazepine.
364. 3-Methyl-4-p-cyclohexyloxyphenoxy-hexahydroazepine.
365. 3-Methyl-4-o-trifluoromethylphenoxy-hexahydroazepine.
366. 3-Methyl-4-m-trifluoromethylphenoxy-hexahydroazepine.
367. 3-Methyl-4-p-trifluoromethylphenoxy-hexahydroazepine.
368. 3-Methyl-4-o-cyanophenoxy-hexahydroazepine.
369. 3-Methyl-4-m-cyanophenoxy-hexahydroazepine.
370. 3-Methyl-4-p-cyanophenoxy-hexahydroazepine.
371. 3-Methyl-4-o-methylthiophenoxy-hexahydroazepine.
372. 3-Methyl-4-m-methylthiophenoxy-hexahydroazepine.
373. 3-Methyl-4-p-methylthiophenoxy-hexahydroazepine.
374. 3-Methyl-4-p-ethylthiophenoxy-hexahydroazepine.
375. 3-Methyl-4-p-isobutylthiophenoxy-hexahydroazepine.
376. 3-Methyl-4-o-trifluoromethylthiophenoxy-hexahydroazepine.
377. 3-Methyl-4-m-trifluoromethylthiophenoxy-hexahydroazepine.
378. 3-Methyl-4-p-trifluoromethylthiophenoxy-hexahydroazepine.
379. 3-Methyl-4-o-hydroxyphenoxy-hexahydroazepine.
380. 3-Methyl-4-m-hydroxyphenoxy-hexahydroazepine.
381. 3-Methyl-4-p-hydroxyphenoxy-hexahydroazepine.
382. 3-Methyl-4-o-acetoxyphenoxy-hexahydroazepine.
383. 3-Methyl-4-m-acetoxyphenoxy-hexahydroazepine.
384. 3-Methyl-4-p-acetoxyphenoxy-hexahydroazepine.
385. 3-Methyl-4-p-propionyloxyphenoxy-hexahydroazepine.
386. 3-Methyl-4-p-butyryloxyphenoxy-hexahydroazepine.
387. 3-Methyl-4-p-valeryloxyphenoxy-hexahydroazepine.
388. 3-Methyl-4-p-hexanoyloxyphenoxy-hexahydroazepine.
389. 3-Methyl-4-p-heptanoyloxyphenol-hexahydroazepine.
390. 3-Methyl-4-(3,4-dimethoxy-phenoxy)-hexahydroazepine.
391. 3-Methyl-4-(2-methoxy-5-trifluoromethyl-phenoxy)-hexahydroazepine.
392. 3-Methyl-4-(2-hydroxy-4-chloro-phenoxy)-hexahydroazepine.
393. 3-Methyl-4-(2-heptanoyloxy)-4-chloro-phenoxy)-hexahydroazepine.
394. 3-Methyl-4-(2-decanoyloxy-4-chloro-phenoxy)-hexahydroazepine.
395. 1,3-Dimethyl-4-phenoxy-hexahydroazepine.
396. 1,3-Dimethyl-4-o-fluorophenoxy-hexahydroazepine.
397. 1,3-Dimethyl-4-m-fluorophenoxy-hexahydroazepine.
398. 1,3-Dimethyl-4-p-fluorophenoxy-hexahydroazepine, 2 isomers, b.p. 80°-81°/0.03 mm and b.p. 85°-86°/0.03 mm.
399. 1,3-Dimethyl-4-o-chlorophenoxy-hexahydroazepine.
400. 1,3-Dimethyl-4-m-chlorophenoxy-hexahydroazepine.
401. 1,3-Dimethyl-4-p-chlorophenoxy-hexahydroazepine.
402. 1,3-Dimethyl-4-o-bromophenoxy-hexahydroazepine.
403. 1,3-Dimethyl-4-m-bromophenoxy-hexahydroazepine.
404. 1,3-Dimethyl-4-p-bromophenoxy-hexahydroazepine.
405. 1,3-Dimethyl-4-o-tolyloxy-hexahydroazepine.
406. 1,3-Dimethyl-4-m-tolyloxy-hexahydroazepine.
407. 1,3-Dimethyl-4-p-tolyloxy-hexahydroazepine.
408. 1,3-Dimethyl-4-p-ethylphenoxy-hexahydroazepine.
409. 1,3-Dimethyl-4-p-isobutylphenoxy-hexahydroazepine.
410. 1,3-Dimethyl-4-o-methoxyphenoxy-hexahydroazepine.
411. 1,3-Dimethyl-4-m-methoxyphenoxy-hexahydroazepine.
412. 1,3-Dimethyl-4-p-methoxyphenoxy-hexahydroazepine, 2 oily isomers, Rf 0.36 and 0.55.
413. 1,3-Dimethyl-4-p-ethoxyphenoxy-hexahydroazepine.
414. 1,3-Dimethyl-4-p-sec.-butoxyphenoxy-hexahydroazepine.
415. 1,3-Dimethyl-4-p-cyclopropyloxyphenoxy-hexahydroazepine.
416. 1,3-Dimethyl-4-o-cyclopentyloxyphenoxy-hexahydroazepine.
417. 1,3-Dimethyl-4-m-cyclopentyloxyphenoxy-hexahydroazepine.
418. 1,3-Dimethyl-4-p-cyclopentyloxyphenoxy-hexahydroazepine.
419. 1,3-Dimethyl-4-o-cyclohexyloxyphenoxy-hexahydroazepine.
420. 1,3-Dimethyl-4-m-cyclohexyloxyphenoxy-hexahydroazepine.
421. 1,3-Dimethyl-4-p-cyclohexyloxyphenoxy-hexahydroazepine.

422. 1,3-Dimethyl-4-o-trifluoromethylphenoxy-hexahydroazepine.
423. 1,3-Dimethyl-4-m-trifluoromethylphenoxy-hexahydroazepine.
424. 1,3-Dimethyl-4-p-trifluoromethylphenoxy-hexahydroazepine, Rf 0.5.
425. 1,3-Dimethyl-4-o-cyanophenoxy-hexahydroazepine.
426. 1,3-Dimethyl-4-m-cyanophenoxy-hexahydroazepine.
427. 1,3-Dimethyl-4-p-cyanophenoxy-hexahydroazepine.
428. 1,3-Dimethyl-4-o-methylthiophenoxy-hexahydroazepine.
429. 1,3-Dimethyl-4-m-methylthiophenoxy-hexahydroazepine.
430. 1,3-Dimethyl-4-p-methylthiophenoxy-hexahydroazepine, 2 oily isomers, Rf 0.50 and 0.31.
431. 1,3-Dimethyl-4-p-ethylthiophenoxy-hexahydroazepine.
432. 1,3-Dimethyl-4-p-isobutylthiophenoxy-hexahydroazepine.
433. 1,3-Dimethyl-4-o-trifluoromethylthiophenoxy-hexahydroazepine.
434. 1,3-Dimethyl-4-m-trifluoromethylthiophenoxy-hexahydroazepine.
435. 1,3-Dimethyl-4-p-trifluoromethylthiophenoxy-hexahydroazepine.
436. 1,3-Dimethyl-4-o-hydroxyphenoxy-hexahydroazepine.
437. 1,3-Dimethyl-4-m-hydroxyphenoxy-hexahydroazepine.
438. 1,3-Dimethyl-4-p-hydroxyphenoxy-hexahydroazepine.
439. 1,3-Dimethyl-4-o-acetoxyphenoxy-hexahydroazepine.
440. 1,3-Dimethyl-4-m-acetoxyphenoxy-hexahydroazepine.
441. 1,3-Dimethyl-4-p-acetoxyphenoxy-hexahydroazepine.
442. 1,3-Dimethyl-4-p-propionyloxyphenoxy-hexahydroazepine.
443. 1,3-Dimethyl-4-p-butyryloxyphenoxy-hexahydroazepine.
444. 1,3-Dimethyl-4-p-valeryloxyphenoxy-hexahydroazepine.
445. 1,3-Dimethyl-4-p-hexanoyloxyphenoxy-hexahydroazepine.
446. 1,3-Dimethyl-4-p-heptanoyloxyphenoxy-hexahydroazepine.
447. 1,3-Dimethyl-4-(3,4-dimethoxy-phenoxy)-hexahydroazepine.
448. 1,3-Dimethyl-4-(2-methoxy-5-trifluoromethyl-phenoxy)-hexahydroazepine.
449. 1,3-Dimethyl-4-(2-hydroxy-4-chloro-phenoxy)-hexahydroazepine.
450. 1,3-Dimethyl-4-(2-heptanoyloxy-4-chloro-phenoxy)-hexahydroazepine.
451. 1,3-Dimethyl-4-(2-decanoyloxy-4-chloro-phenoxy)-hexahydroazepine.

EXAMPLES 452 to 457

The following compounds are obtained analogously to Example 1 from p-chlorophenol and 1-ethyl-, 1-n-butyl-, 1-vinyl-, 1-allyl-, 1-cyclopropylmethyl- or 1-benzyl-2-(2-bromoethyl)-piperidine:
452. 1-Ethyl-2-(2-p-chlorophenoxyethyl)-piperidine.
453. 1-n-Butyl-2-(2-p-chlorophenoxyethyl)-piperidine.
454. 1-Vinyl-2-(2-p-chlorophenoxyethyl)-piperidine.
455. 1-Allyl-2-(2-p-chlorophenoxyethyl)-piperidine, Rf 0.695 (CHCl3/triethylamine, 8:2)
456. 1-Cyclopropylmethyl-2-(2-p-chlorophenoxyethyl)-piperidine, Rf 0.735 (CHCl3/triethylamine,, 8:2).
457. 1-Benzyl-2-(2-p-chlorophenoxyethyl)-piperidine.

EXAMPLE 458

200 ml of 50% aqueous sodium hydroxide solution and 1 g of triethylbenzylammonium chloride are added to a solution of 12.8 g of p-chlorophenol in 100 ml of CH2Cl2; 16.2 g of 1-methyl-2-(2-chloroethyl)-piperidine are added dropwise, while stirring; and the reaction mixture is stirred for a further one hour. After customary working up, 1-methyl-2-(2-p-chlorophenoxyethyl)-piperidine is obtained. Hydrochloride, m.p. 139°–140°.

EXAMPLE 459

A solution of 30.3 g. of 2-(2-m-trifluoromethylphenoxy-ethyl)-pyridine hydrochloride (obtainable by reacting sodium-m-trifluoromethylphenolate with 2-(2-chloroethyl)pyridine) in 1 liter of ethanol is hydrogenated on 1 g of PtO2 at 20° and 1 atmosphere until the reaction has ceased. The reaction mixture is filtered, the filtrate is evaporated and the resulting 2-(2-m-trifluoromethylphenoxy-ethyl)piperidine hydrochloride is recrystallized from isopropanol. m.p. 152°–153°.

EXAMPLE 460

A solution of 36.1 g of 1-methyl-2-(2-p-benzyloxyphenoxyethyl)-piperidine hydrochloride (m.p. 164°; obtainable from Na p-benzyloxyphenolate and 1-methyl-2-(2-chloroethyl)piperidine) in 400 ml of methanol is hydrogenated on 3 g of 5% Pd-C at 20° and 1 atmosphere until the reaction has ceased. The reaction mixture is filtered, the filtrate is evaporated and 1-methyl-2-(2-p-hydroxyphenoxyethyl)-piperidine hydrochloride, m.p. 182°, is obtained.

EXAMPLE 461

30 g of formic acid are added dropwise to 23.9 g of 2-(2-p-chlorophenoxyethyl)-piperidine, while stirring and cooling, and 7 g of 25% formaldehyde solution are then added dropwise at 20°. The reaction mixture is heated on a water bath until the evolution of gas has ceased and is cooled, poured onto ice and worked up in the customary manner and this gives 1-methyl-2-(2-p-chlorophenoxyethyl)-piperidine. Hydrochloride, m.p. 139°–140°.

EXAMPLE 462

12 g of allyl bromide and 26 g of anhydrous potassium carbonate are added to a solution of 23.9 g of 2-(2-p-chlorophenoxy-ethyl)-piperidine in 1 liter of absolute toluene, the mixture is boiled for 20 hours, cooled, poured into water and worked up in the customary manner and this gives 1-allyl-2-(2-p-chlorophenoxyethyl)-piperidine. Rf 0.7 (CHCl3/triethylamine).

EXAMPLES 463 to 466

The following compounds are obtained analogously to Example 462, with n-butyl iodide, cyclopropylmethyl chloride or benzyl bromide:
463. 1-n-Butyl-2-(2-p-chlorophenoxyethyl)-piperidine.
464. 1-Cyclopropylmethyl-2-(2-p-chlorophenoxyethyl)-piperidine.
465. 1-Cyclopropylmethyl-2-(2-p-fluorophenoxyethyl)-piperidine, Rf 0.5.

466. 1-Benzyl-2-(2-p-chlorophenoxyethyl)-piperidine.

EXAMPLE 467

2-(2-p-Chlorophenoxyethyl)-piperidine, hydrochloride, m.p. 220°, is obtained analogously to Example 460 by hydrogenolysis of 1-benzyl-2-(2-p-chlorophenoxyethyl)-piperidine.

EXAMPLE 468

23.5 g of 1,3-dimethyl-4-p-hydroxyphenoxy-hexahydroazepine are dissolved in 100 ml of absolute ethanol, 200 ml of 0.5 N ethanolic KOH are added, the reaction mixture is stirred for one hour at 20° and evaporated and the residue is taken up in 250 ml of absolute DMF. 12.6 g of dimethyl sulfate are added in portions, while stirring. The mixture is boiled for 2 hours and evaporated and the residue is worked up in the customary manner, giving 1,3-dimethyl-4-p-methoxyphenoxy-hexahydroazepine, 2 oily isomers, Rf 0.36 and 0.55.

EXAMPLE 469

13 g of heptanoic acid are dissolved in 10 ml of dry DMF, 16.2 g of carbonyldiimidazole and then a solution of 27 g of 1-methyl-2-[2-(2-hydroxy-4-chlorophenoxy)-ethyl]piperidine in 50 ml of dry THF are added and the mixture is stirred overnight at 20°. The reaction mixture is evaporated and the residue is treated with ethereal hydrochloric acid. The 1-methyl-2-[2-(2-heptanoyloxy-4-chlorophenoxy)ethyl]piperidine hydrochloride which has precipitated is filtered off and dried.

The examples which follow relate to pharmaceutical formulations which contain amines of the formula I of their acid addition salts:

EXAMPLE A: TABLETS

A mixture of 1 kg of 1-methyl-2-(2-p-chlorophenoxyethyl)-piperidine hydrochloride, 4 kg of lactose, 1.2 kg of potato starch, 0.2 kg of talc and 0.1 kg of magnesium stearate is compressed to tablets in the customary manner, so that each tablet contains 10 mg of active ingredient.

EXAMPLE B: DRAGEES

Tablets are pressed analogously to Example A and these are then coated in the customary manner with a coating of sucrose, potato starch, talc, tragacanth and dyestuff.

EXAMPLE C: CAPSULES 2 kg of 1-methyl-2-(2-p-chlorophenoxyethyl)-piperidine hydrochloride are filled into hard gelatine capsules in the customary manner, so that each capsule contains 20 mg of the active ingredient.

EXAMPLE D: AMPOULES

A solution of 1 kg of 1-methyl-2-(2-p-chlorphenoxyethyl)-piperidine hydrochloride in 30 liters of twice distilled water is sterile-filtered, filled into ampoules and lyophilized under sterile conditions and the ampoules are sealed under sterile conditions. Each ampoule contains 10 mg of active ingredient.

Tablets, dragees, capsules and ampoules which contain one or more of the other active compounds of formula I and/or their physiologically acceptable acid addition salts are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A phenoxyalkylamine of the formula

wherein Ar is phenyl or phenyl which is monosubstituted or disubstituted by F, Cl, Br, alkyl or alkoxy each of 1-4 carbon atoms, cycloalkoxy of 3-6 carbon atoms, $CF_3$, CN, alkylthio of 1-4 carbon atoms, $SCF_3$, OH and/or alkanoyloxy with 1-10 carbon atoms; R is $(1-R^1-2-pyrrolidyl)—CH_2—CHR^2$, $(1-R^1-2-piperidyl)—CH_2—CHR^2—$ or $1-R^1-3-Z-4-hexahydroazepinyl$; $R^1$ is H, alkyl or alkenyl each of up to 4 carbon atoms, cyclopropylmethyl or benzyl; $R^2$ is H, alkyl of 1-4 carbon atoms or phenyl; and Z is alkyl of 1-4 carbon atoms with the proviso that Ar is p-fluorophenyl only if R is not 2-(1-methyl-2-piperidyl)-ethyl;

and the physiologically acceptable acid addition salts thereof.

2. 1-Methyl-2-(2-p-chlorophenoxyethyl)-piperidine, a compound of claim 1.

3. 1,3-dimethyl-4-p-methylthiophenoxy-hexahydroazepine; 1,3-dimethyl-4-p-fluorophenoxy-hexahydroazepine; 1,3-dimethyl-4-p-methoxyphenoxy-hexahydroazepine; 1-methyl-2-(2-p-methylthiophenoxyethyl)-piperidine; 2-(2-p-methylthiophenoxyethyl)-piperidine; or 1-methyl-2-(2-m-trifluoromethylphenoxyethyl)-pyrrolidine, compounds of claim 1.

4. The compounds of claim 1, wherein R is 2-(2-pyrrolidyl)-ethyl, 2-(1-methyl-2-pyrrolidyl)-ethyl, 2-(2-piperidyl)-ethyl or 2-(1-methyl-2-piperidyl)-ethyl.

5. A pharmaceutical composition comprising an antidepressantly effective amount of a compound of claim 1 and a pharmaceutically acceptable carrier.

6. A method of treating depression in mammals which comprises administering to the mammal an antidepressantly effective amount of a compound of claim 1.

* * * * *